United States Patent
Mlinar et al.

(10) Patent No.: US 8,043,274 B2
(45) Date of Patent: Oct. 25, 2011

(54) DISPOSABLE UNDERGARMENT WITH STRETCH AREAS FOR OPTIMAL FIT

(75) Inventors: Joseph Andrew Mlinar, Appleton, WI (US); Wendy L. Hamilton, Neenah, WI (US); Julie A. Paveletzke, Appleton, WI (US); Mary F. Kutchenriter, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 849 days.

(21) Appl. No.: 11/951,029

(22) Filed: Dec. 5, 2007

(65) Prior Publication Data

US 2009/0149827 A1 Jun. 11, 2009

(51) Int. Cl.
*A61F 13/15* (2006.01)

(52) U.S. Cl. ............ 604/385.22; 604/385.24; 604/385.3

(58) Field of Classification Search ............. 604/385.22, 604/385.24, 385.3
See application file for complete search history.

(56) References Cited

U.S. PATENT DOCUMENTS

| | | | |
|---|---|---|---|
| 3,424,162 A | 1/1969 | Parravicini | |
| 4,205,679 A | 6/1980 | Repke et al. | |
| 4,610,681 A | 9/1986 | Strohbeen et al. | |
| 4,641,381 A | 2/1987 | Heran et al. | |
| 4,646,362 A | 3/1987 | Heran et al. | |
| 4,690,681 A | 9/1987 | Haunschild et al. | |
| 4,720,415 A | 1/1988 | Vander Wielen et al. | |
| 4,756,709 A | 7/1988 | Stevens | |
| 4,847,134 A | 7/1989 | Fahrenkrug et al. | |
| 4,940,464 A * | 7/1990 | Van Gompel et al. ........ | 604/396 |
| 5,026,364 A | 6/1991 | Robertson | |
| 5,114,781 A | 5/1992 | Morman | |
| 5,116,662 A | 5/1992 | Morman | |
| 5,269,775 A * | 12/1993 | Freeland et al. ......... | 604/385.22 |
| 5,352,216 A | 10/1994 | Shiono et al. | |
| 5,376,198 A | 12/1994 | Fahrenkrug et al. | |
| 5,685,874 A * | 11/1997 | Buell et al. .................... | 604/396 |
| 5,846,232 A | 12/1998 | Serbiak et al. | |
| 5,899,895 A * | 5/1999 | Robles et al. ............ | 604/385.29 |
| 5,993,431 A * | 11/1999 | McFall et al. ............ | 604/385.24 |
| 6,262,331 B1 | 7/2001 | Nakahata et al. | |

(Continued)

FOREIGN PATENT DOCUMENTS

EP 1201212 5/2002

(Continued)

OTHER PUBLICATIONS

Abstract of JP 03224559 published Oct. 3, 1991.

(Continued)

*Primary Examiner* — Lynne Anderson
(74) *Attorney, Agent, or Firm* — Dority & Manning, P.A.

(57) ABSTRACT

A disposable incontinent underwear product can comprise areas having different stretch characteristics and thereby fit persons of varying body shape in a more comfortable and/or visually appealing manner. Additionally, in some embodiments, the different areas of stretch can aid in positioning absorbent components, such as an absorbent insert or core that is included in the undergarment to absorb body exudates. For example, a garment may feature at vertical stretch in an area above the crotch and below the waist while featuring horizontal stretch at the hip areas at its front and back sides. As another example, a garment may feature horizontal stretch across the front of the garment and vertical stretch across the back of the garment in areas above the crotch and below the waist. In some embodiments, the crotch also features horizontal, vertical, or biaxial stretch.

17 Claims, 3 Drawing Sheets

U.S. PATENT DOCUMENTS

| | | |
|---|---|---|
| 6,375,646 B1 | 4/2002 | Widlund et al. |
| 6,468,630 B1 | 10/2002 | Mishima et al. |
| 6,478,785 B1 * | 11/2002 | Ashton et al. ............ 604/385.01 |
| 6,482,191 B1 | 11/2002 | Roe et al. |
| 6,502,250 B2 | 1/2003 | Suga et al. |
| 6,570,056 B1 | 5/2003 | Tanzer et al. |
| 6,579,274 B1 | 6/2003 | Morman et al. |
| 6,605,070 B2 | 8/2003 | Ludwig et al. |
| 6,620,146 B2 | 9/2003 | Gibbs |
| 6,627,564 B1 | 9/2003 | Morman et al. |
| 6,632,212 B1 | 10/2003 | Morman et al. |
| 6,840,928 B2 * | 1/2005 | Datta et al. ............... 604/385.22 |
| 6,842,191 B1 | 1/2005 | Smith |
| 6,964,720 B2 | 11/2005 | Schneider et al. |
| 7,150,730 B2 | 12/2006 | Hasler et al. |
| 7,220,335 B2 | 5/2007 | Van Gompel et al. |
| 2002/0165516 A1 * | 11/2002 | Datta et al. ............... 604/385.16 |
| 2003/0125696 A1 | 7/2003 | Morman et al. |
| 2004/0002689 A1 | 1/2004 | Igaue et al. |
| 2004/0186452 A1 | 9/2004 | Sandin et al. |
| 2006/0089615 A1 | 4/2006 | Saito |
| 2007/0048497 A1 | 3/2007 | Zhou et al. |
| 2007/0117481 A1 | 5/2007 | Day et al. |

FOREIGN PATENT DOCUMENTS

| | | |
|---|---|---|
| EP | 1578326 | 9/2005 |
| EP | 1578330 | 9/2005 |
| EP | 1578333 | 9/2005 |
| JP | 03224559 | 10/1991 |
| JP | 03251245 | 11/1991 |
| JP | 11276523 | 10/1999 |
| JP | 2001258931 | 9/2001 |
| JP | 2001293030 | 10/2001 |
| JP | 05120516 | 5/2005 |
| WO | WO 9616624 | 6/1996 |
| WO | WO 9739711 | 10/1997 |
| WO | WO 9743994 | 11/1997 |
| WO | WO 9900095 | 1/1999 |
| WO | WO 0047152 | 8/2000 |
| WO | WO 0143968 | 6/2001 |
| WO | WO 02085273 | 10/2002 |
| WO | WO 03037213 | 5/2003 |
| WO | WO 03043530 | 5/2003 |
| WO | WO 2004012640 | 2/2004 |
| WO | WO 2005065609 | 7/2005 |
| WO | WO 2006093443 | 9/2006 |

OTHER PUBLICATIONS

Abstract of JP 03251245 published Nov. 8, 1991.
Abstract of JP 11276523 published Oct. 12, 1999.
Abstract of JP2001258931 published Sep. 25, 2001.
Abstract of JP2001293030 published Oct. 23, 2001.
Abstract of JP 2005120516 published May 12, 2005.

* cited by examiner

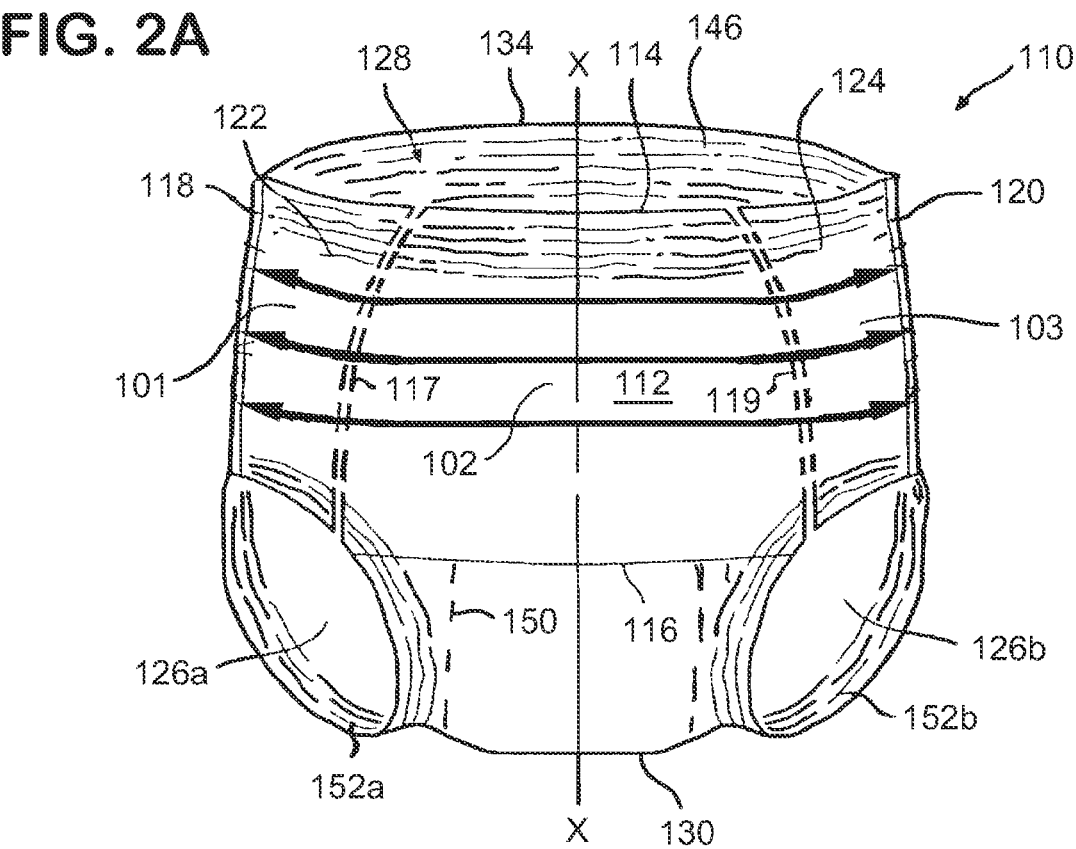
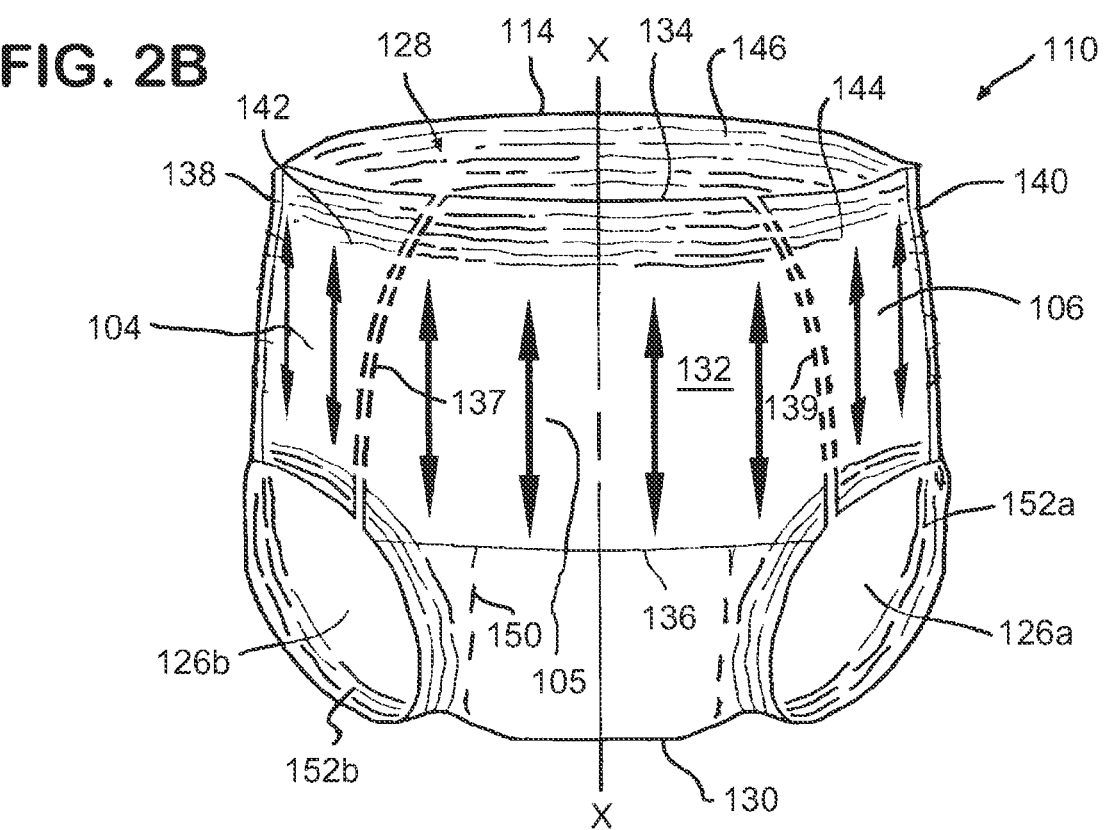

DISPOSABLE UNDERGARMENT WITH STRETCH AREAS FOR OPTIMAL FIT

BACKGROUND

Pant-like disposable undergarments for absorbing human exudates, such as fecal matter, urine and/or other material can appear similar in size and shape to regular cloth underwear that is designed to be laundered and reused one or more times. A disposable undergarment is intended to be worn by persons, such as infants, toddlers, or adults, for single use or temporary use and is meant to be disposed of after being used once instead of being laundered, dry cleaned, or otherwise made ready for reuse. Examples of disposable undergarments include infant diapers, training pants, adult incontinence garments, feminine hygiene pants, and the like.

Currently, some disposable undergarments, such as disposable incontinent underwear products, feature limited stretch ability. For instance, an undergarment may stretch horizontally at the waist area through use of one or more elastic strands, such as LYCRA strands. However, such limited stretch may not provide optimal fit for all persons or all situations.

SUMMARY

A disposable incontinent underwear product made in accordance with one or more aspects of the present subject matter can comprise areas having different stretch characteristics. A disposable incontinent underwear product or other disposable undergarment may thereby fit persons of varying body shape in a more comfortable and/or visually appealing manner. Additionally, in some embodiments, the different areas of stretch can aid in positioning absorbent components, such as an absorbent insert or core that is included in the undergarment to absorb body exudates.

In some embodiments, a disposable incontinent underwear product can comprise a front panel having a top and bottom end and two respective sides and a back panel also having a top and bottom end and two respective sides. The front panel can define a front waist region of a disposable incontinent underwear product at the top end, while the back panel can define a back waist region of the garment at top end of the back panel. The product can further comprise an absorbent insert or assembly positioned in a crotch region of the disposable incontinent underwear product. The crotch region can comprise the bottom ends of the front and back panels. For example, the bottom ends of the front and back panel may be connected by one or more pieces of material therebetween and/or by the absorbent assembly. In other embodiments, the bottom ends of the front and back panel may be shaped and connected directly to form the crotch region.

Furthermore, the front and back panels can be joined at respective sides to define hip regions of the disposable incontinent underwear product. For example, the product may come pre-assembled or may be assembled by a wearer or other end user by joining the sides of the front and back panels so that the front and back waist regions define a waist opening and the sides of the crotch region (and also portions of the front and back panels) define leg openings.

In some embodiments, a portion of the front panel lying between the crotch region and the front and waist region can be stretchable in a vertical direction, while portions of the front panel defining the hip regions are stretchable in a horizontal direction. Similarly, a portion of the back panel lying between the crotch region and back waist region can be stretchable in a vertical direction while portions of the back panel defining the hip regions may be stretchable in a horizontal direction.

Generally speaking, in the present specification, a "vertical" direction refers to the direction that is perpendicular to the axis of the waist edge of the garment when laid flat, with the waist edge of the garment extending in a generally horizontal direction.

In some embodiments, a portion of the front panel lying between the crotch region and the front waist region can be stretchable in a horizontal direction, while a portion of the back panel lying between the crotch region and the back waist region is stretchable in a vertical direction. For instance, in some embodiments, the portion of the front panel that is stretchable in the horizontal direction extends substantially across the entirety of the front panel from each side of the front panel, while the portion of the back panel that is stretchable in the vertical direction extends substantially across the back panel from both sides of the back panel.

In some embodiments, regardless of the particular directions of stretch, the portions of the front and back panels which are stretchable in the horizontal direction are not substantially stretchable in the vertical direction, while portions that are stretchable in the vertical direction are substantially not stretchable in the horizontal direction. Furthermore, in some embodiments, the front, back, and/or other panels may comprise elastic material that is embossed to impart the respective horizontal, vertical, and/or other stretch characteristics of the product.

In some embodiments, the crotch region may be stretchable in at least one of the horizontal and vertical directions, or may be stretchable in both the horizontal and vertical direction. In some embodiments, the product can comprise an elastic waistband stretchable in the horizontal direction and positioned at the top ends of the front and back panels.

In some embodiments, the front panel and/or the back panel may comprise multiple pieces of material. For example, the portion of the front (or back) panel between the waist region and the crotch region may comprise a separate piece of material from the portion of the front (or back) panel comprising one or more of the hip regions. For instance, a garment may be formed of a front portion, back portion, and two or more hip portions joined together, along with an absorbent insert, other components such as elastics, covers, etc. In some embodiments, the front and back panels (including or exclusive of the hip regions) may comprise a unitary piece of material extending from the front waist region to the back waist region.

In some embodiments, at least one of the front and back panels (or both) comprise at least one tear line substantially parallel to a side edge of the garment. For example, a tear line can comprise an area wherein the material has been conditioned to facilitate separation of the material along the tear line. For instance, the garment may be perforated, cut, or otherwise processed so that the garment can be separated and removed more readily. The tear lines may be positioned in the hip region(s) in some embodiments, and may be outside the hip region or at the boundary between the hip region and front portion (and/or the boundary between the hip region and the back portion) of the garment, for example.

In some embodiments, the article may comprise one or more inner layers which contact the body of a wearer of the product and one or more layers positioned outside an inner layer and opposite the inner layer. For example, the product may comprise an outer cover, with the front and back panels comprising a portion of the outer cover. In some embodiments, the front and back panels may comprise stretchable areas, while the inner layer or layers do not comprise stretchable material (or the stretch characteristics of the inner layer differ from the front and/or back panels).

Other features and aspects of the present invention are discussed in greater detail below.

BRIEF DESCRIPTION OF THE DRAWINGS

A full and enabling disclosure including the best mode of practicing the appended claims and directed to one of ordinary skill in the art is set forth more particularly in the remainder of the specification. The specification makes reference to the appended figures, in which:

FIG. 2A is a front side view of another exemplary disposable undergarment;

FIG. 2B is a back side view of the exemplary disposable undergarment shown in FIG. 2A.

Use of like reference numerals is intended to illustrate like or analogous components.

DETAILED DESCRIPTION

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the present disclosure includes modifications and variations as come within the scope of the appended claims and their equivalents.

Figure 1A:
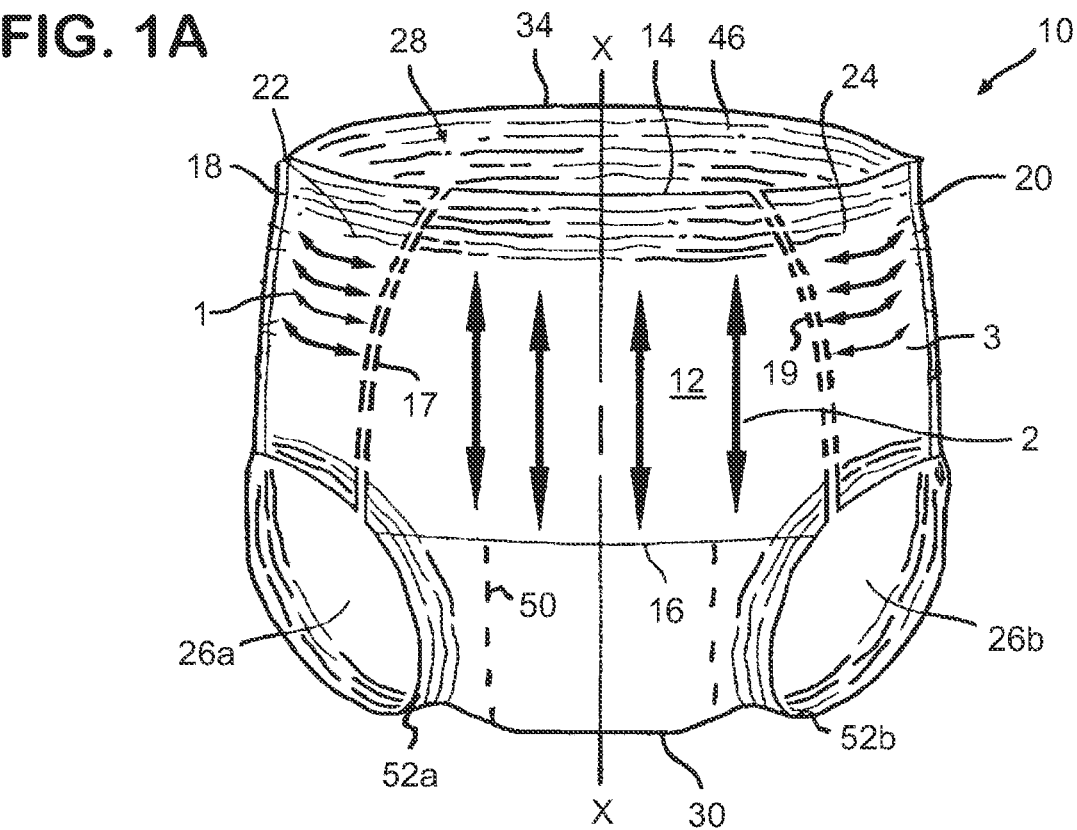
FIG. 1A is a front side view of an exemplary disposable undergarment.
Figure 1B:
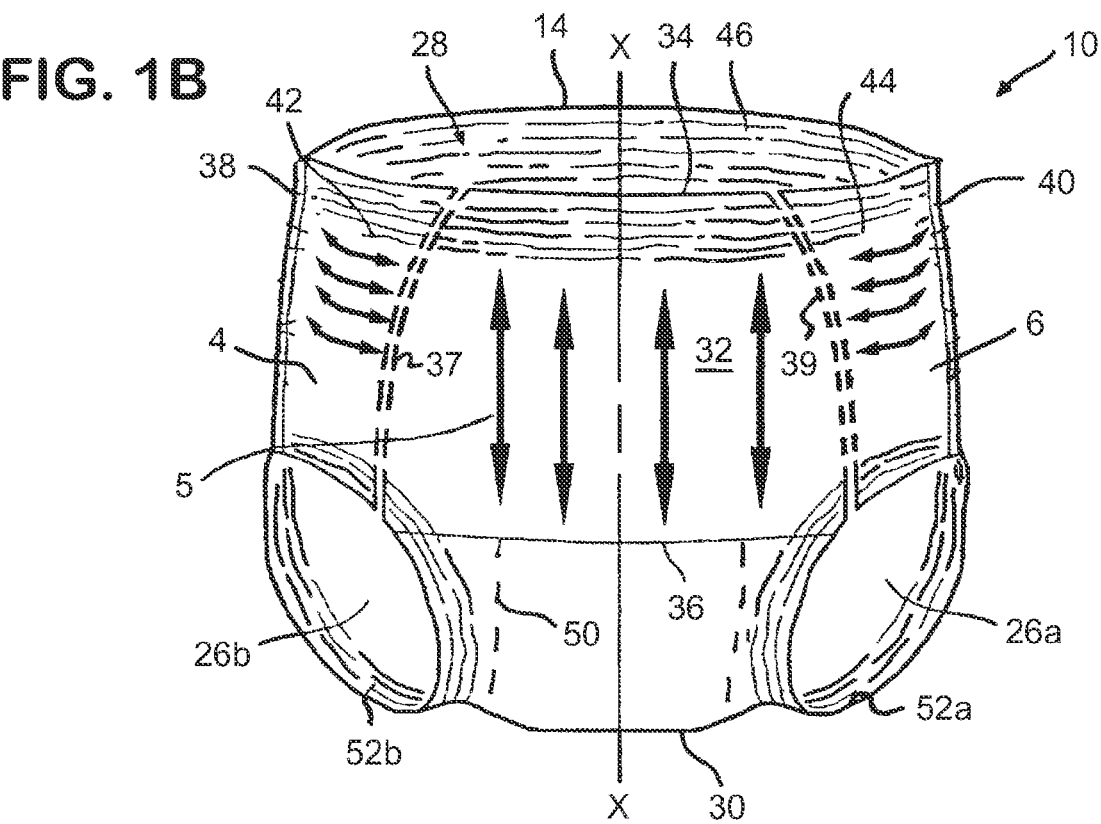
FIG. 1B is a back side view of the exemplary disposable undergarment shown in FIG. 1A.

FIGS. 1A and 1B show a pant-like disposable garment 10 constructed in accordance with aspects of the present subject matter. In this example, garment 10 comprises a front panel 12, a back panel 32 joined and arranged to define a waist opening 28 and leg openings 26a and 26b. Garment 10 as shown in FIGS. 1A and 1B is positioned generally in the shape in which the garment would be found when worn by a user. The line x-x defines an axis extending in the vertical direction. References herein to a "horizontal" direction refer to a direction perpendicular to line x-x.

Garment 10 may be constructed according any suitable technique or techniques known to one of skill in the art. For example, garment 10 may comprise a chassis that includes one or more inner or body-side layers that contact the skin of a wearer of the article and one or more outer layers or covers positioned alongside the body-side layers.

In this example, product 10 comprises a front panel 12 and a back panel 32. Front panel 12, best visible in FIG. 1A, includes a top end 14, which also defines a front waist region of garment 10, a first side 18, a second side 20 opposite the first side and a bottom end 16. FIG. 1A also illustrates the front sides 22 and 24 of hip regions of the garment, which will be discussed in further detail below. Dashed lines 17 and 19 indicate the border between the front of the garment and the portion of the garment identified as the hip areas in this example. In some embodiments, front panel 12 may comprise several sub-panels, such as separate pieces for hip regions such as 22 and 24. In this example, garment 10 further includes leg elastics 52A and 52B which are included to ensure that the garment fits around a wearer's legs when extended through leg openings 26A and 26B. Leg openings may be defined by a combination of leg elastics 52 and crotch elastics 53 (not shown in FIGS. 1-2). For instance, crotch elastics 53 may be positioned along the side perimeter of the absorbent insert 50 in some embodiments.

In some embodiments, dashed lines 17/19 and/or 37/39 may represent perforations, cuts, or other points wherein the garment is configured to be easily separated by a wearer. For instance, if side edges 18, 20, 38, and 40 are permanently bonded together, the garment may be removed in the same manner as conventional undergarments. However, separation points (e.g. perforations) may allow a user and/or caregiver to tear the garment off for easier removal. In some embodiments, tear lines/perforations 17, 19, 37, and 39 are parallel or substantially parallel to the side seam bonds joining the front and back of the garment.

In addition to the stretch characteristics that will be discussed below, in some embodiments, garment 10 can include an elastic waist band 46 comprising any suitable material, such as one or more elastic strand, ribbons, or other structures that aid in retaining the garment on a wearer. However, although shown in this example, not all embodiments feature an elastic (or other) waist band 46. For instance, in some embodiments, the stretch characteristics of the remainder of the garment may be sufficient to hold the garment in place without the need for a waistband.

Turning to FIG. 1B, a rear side view of garment 10 is presented. Back panel 32 includes a top end 34 defining a back waist region, a bottom end 36, and two opposite sides 38 and 40 which are joined to corresponding front side edges 18 and 20. FIG. 1B illustrates back sides 42 and 44 of hip regions of the garment, which, as indicated by dashed lines 37 and 39, may comprise lateral portions of back panel 32 or separate components in some embodiments.

Garment 10 further includes a crotch region generally denoted as 30 and comprising bottom ends 16 and 36 of front panel 12 and back panel 32, respectively. Generally speaking, the crotch region refers to the portion of the garment which extends between the lower abdomen and back side of a user between the user's legs when the article is worn. As is known in the art, one or more absorbent assemblies or inserts 50 can be positioned in the crotch region so as to absorb exudates such as urine, perspiration, excrement, feces, menses, menstrual fluid and other liquid and/or solid waste from a user. Depending upon the configuration of garment 10, crotch region 30 may comprise material extending from bottom end 16 of front panel 12 to bottom end 36 of back panel 32, or may simply comprise lower ends of front panel 12 and back panel 32 joined together in any suitable manner. Absorbent assembly may extend beyond crotch region 30 and past bottom end 16 of front panel 12 and/or past bottom end 36 of back panel 32 in some embodiments.

The garments of the present subject matter can be constructed using any suitable materials or architecture. For instance, the front and/or back panels 12 and 32, respectively, can be formed from a single piece of material or they can be a laminate of two or more layers. The layers of the laminate can be of the same material or different material. The front and/or back panels 12 and 32, respectively, can be formed from a breathable or a non-breathable material. A polyolefin, such as polypropylene or polyethylene can be used as well as spunbond or a bonded carded web. A metallocene polypropylene works very well since it has a soft feel and can be easily ultrasonically bonded to itself. However, in other embodiments, pressure bonding may be used instead of ultrasonic bonding.

Although not illustrated in detail herein, elastics, such as leg elastics 52 and/or other elastics used in the garment, can be formed between layers in multi-layer embodiments. For instance, in an embodiment comprising a laminate structure, two or more strands of elastic 36 can be sandwiched between layers. As another example, if an elastic waistband 46 is included in the product, two to ten strands of elastic can be utilized in the front panel 12 to form waistband 46. For instance, the elastic strands can be formed from LYCRA. LYCRA is a trademark of Invista, Inc., of Wichita, Kans. As another example, the elastic strands may be formed from KRATON polymers available from Kraton Polymers, LLC of Houston, Tex. The diameter and/or cross-sectional configuration of the elastic strands, the decitex (weight in grams per 10,000 meters of a strand) of the elastic strands, and tension imparted into the elastic strands can all be varied to the particular product needs.

As was noted above, a disposable undergarment such as exemplary garments 10 (and/or 110, 210 discussed below) can include an absorbent assembly or insert 50 (150, 250 below). In some embodiments, the absorbent assembly 50 includes a liquid pervious bodyside liner, a liquid-impervious outer cover, and an absorbent positioned therebetween. The liquid pervious bodyside liner is located nearest to the human body, adjacent to the skin of the user, and can be formed from a woven or non-woven material that will readily allow liquid or fluids to pass therethrough. The bodyside liner is normally a very thin web that can be formed from natural or synthetic fibers, with or without apertures formed therein. A spunbond and a bonded carded web are two exemplary materials that work well as a bodyside liner. "Spunbond" is manufactured and sold commercially by Kimberly-Clark Corporation having an office at 401 North Lake Street, Neenah, Wis. 54956. The liquid-impervious outer cover is located on the exterior of the disposable undergarment 10, away from the skin of the user. The liquid-impervious outer cover is formed from a material which will restrict fluid from penetrating or passing therethrough so as to prevent the outer clothing of the wearer from becoming soiled.

Retuning to the exemplary absorbent assembly 50, the absorbent is sealed within the liquid pervious bodyside liner and the liquid-impervious outer cover. The absorbent can be formed from natural or synthetic materials such as, for example, cellulosic fibers, wood pulp, textile fibers or other absorbent materials known to those skilled in the art. Superabsorbents, in solid form and in the shape of small particles, granules, flakes, etc., can be mixed in with the absorbent material to increase the absorbent capacity.

In embodiments comprising an outer cover, the outer cover can have a soft feel so as not to chafe the inner thighs of the wearer. The outer cover can also be formed from natural or synthetic fibers. The outer cover can be formed from a material that is not noisy when squeezed or wrinkled so that the disposable undergarment 10 remains discreet. The outer cover can also be formed from a breathable material. The outer cover can further be formed from a laminate where one layer of the laminate is liquid-impervious. Examples of various materials that can be used as the outer cover include a polyolefin, such as polypropylene or polyethylene; a liquid impervious layer bonded to a spunbond; and a thermoplastic material bonded to a spunbond. Other materials known to those skilled in the art can also be utilized. However, in other embodiments, front panel 12 and back panel 32 may be formed using embossed elastic material having a soft, cottony appearance that also functions as an outer cover.

The absorbent assembly 50 can be secured to the front and back panels, 12 and 32 respectively, in a permanent fashion or in a removable fashion to enable a replacement assembly to be later substituted. The pair of end edges of the absorbent assembly can be secured to the front and back panels, 12 and 32 respectively, by any means known to those skilled in the art. Some examples include the use of an adhesive, co-adhesives, glue, ultrasonics, stitching using thread, heat and/or pressure seals, mechanical means, etc. The exact distance the end edges of assembly 50 are spaced from the bottom ends, 16 and 36 respectively, of the front and back panels 12 and 32 can vary to optimize the functionality of the disposable undergarment 10. It should be noted that the distance the end edge of assembly 50 is spaced away from the bottom end 16 of the front panel 12 can be less than, equal to or greater than the distance that the opposite end edge of assembly 50 is spaced away from the bottom end 36 of the back panel 32. For active adults, the absorbent assembly 50 may be positioned such that the end edges are equally spaced from the bottom ends 16 and 36 of the front and back panels, 12 and 32 respectively. For a bedridden person, the absorbent assembly 50 can be positioned closer to the bottom end 36 of the back panel 32 so as to provide added protection against leakage of body fluid from a person lying in a recumbent manner.

Side edges can be joined in any suitable manner. For example, the side edges may be joined using thermal, ultrasonic, adhesive, and/or other bonding. In some embodiments, the side edges may be removably joined, for instance, via suitable adhesives or fasteners, such as hook-and-loop or other fasteners. Additionally, in some embodiments, the interface between the side edges and/or the panel(s) may be configured with perforations or tear lines to facilitate easy removal of the garment via separation of the garment at or near its sides.

As was noted above, in some embodiments of the present subject matter, a pant-like disposable undergarment can provide for better fit through the use of areas of differing stretch characteristics. In this example, garment 10 features six different areas (labeled as 1-6 in FIGS. 1A and 1B) of directional stretch which, in this example, comprise two different types of stretch. Turning first to the front view of garment 10, front hip area 22 and 24 are characterized by horizontal stretch (labeled as 1 and 3), while the portion of front panel 12 between top end 14 and bottom end 16 is characterized by vertical stretch (labeled as 2 in FIG. 1A). Similarly, back hip areas 42 and 44 are characterized by horizontal stretch (labeled as 4 and 6), while the portion of article 10 lying between top end 34 of back panel 32 and bottom end 36 of back panel 32 is characterized by vertical stretch (labeled as 65 in FIG. 1B). Accordingly, the horizontal stretch in the hip area and vertical stretch above the absorbent insert 50 allow the area above the insert to extend upward and create more space for male genitalia and/or provide a more contoured or tailored fit for larger abdomens.

Stretch characteristics may be achieved using any suitable technique or techniques. However, the use of an embossed material can provide both stretch and a soft cottony feel, and thus can provide a more underwear-like product. For instance, the outer cover can comprise a laminate of one or more nonwoven materials with a topographied film or netting having elastic properties that provide the desired stretch characteristics. The topographied film or netting may be formed from an extruded film that is then patterned/embossed by rolls. The ability of the film or netting to stretch can be dependent upon both the structural geometry of the film or netting material an also the polymers making up the film or netting material. Exemplary discussion of formation of topographied films/netting can be found in U.S. patent application Ser. No. 10/581,731, filed Dec. 22, 2003 and entitled BIDIRECTIONAL STRETCH MATERIAL AND LAMINATE MADE THEREFROM, APPLICATIONS THEREOF, AND METHODS OF MAKING SAME, assigned to the present assignee.

The film, netting, and/or other elastic material can be used, for example, as part of a necked bonded laminate or a stretch-bonded laminate. To "neck" or be "necked" refers to a process of tensioning a fabric in a particular direction thereby reducing the dimension of the fabric in the direction perpendicular to the direction of tension. For example, tensioning a nonwoven fabric in the machine direction (MD) causes the fabric to "neck" or narrow in the cross-direction (CD) and give the necked fabric CD stretchability. When the tensioning force is removed, the material can be pulled back to its original dimension (in the direction perpendicular to the direction of tension). "Neck bonding" refers to the process wherein an elastic member is bonded to a non-elastic member while only the non-elastic member is extended or necked so as to reduce its dimension in the direction orthogonal to the extension. "Neck bonded laminate" refers to a composite elastic material made according to the neck bonding process, i.e., the layers are joined together when only the non-elastic layer is in an extended condition.

"Stretch bonded laminate" refers to a composite elastic material made by bonding the elastic material to the other layer(s) when the elastic material is in a stretched state. For example, when a topographied film or netting is used as an elastic base fabric in a stretch-bonded laminate comprising multiple nonwoven layers, one or more corrugations/gathers may occur in the laminate after tension is removed. The gathered laminate will provide a textured fabric that may impart the desired fabric-like look and feel if the laminate is used as the outer cover.

Other embodiments may utilize a necked nonwoven layer bonded to each side of the film, netting, and/or other elastic material. In still further embodiments, the laminate is a stretch necked bonded laminate wherein the elastic film, netting, and/or other material is bonded to a necked nonwoven layer.

Generally speaking, the areas of stretch refer to areas of the garment that are at least extensible in the indicated direction(s), in that the material can extend beyond its original dimensions without breaking when force is applied in the indicated direction(s). In some embodiments, the areas of stretch refer to areas of the garment that exhibit elastic (or elastomeric) properties wherein the areas not only can extend when force is applied in the indicated direction(s), but also return to their original dimensions or approximately their original dimensions once force is no longer applied. A hypothetical example would be a one (1) inch sample of a material which is stretchable to at least 1.50 inches and which, upon release of the stretching force, will recover to a length of not more than 1.25 inches.

Returning to FIGS. 1A and 1B, in this example, the crotch area 30 does not extend. However, in other embodiments, the crotch area could also extend vertically and/or horizontally. The use of stretch, and the degree of stretch can be determined based on factors such as the intended use of the product. For example, too much stretch in the crotch region could cause the material to sag over time due to the weight of fluid or other material in the absorbent assembly 50. However, horizontal, vertical or biaxial stretch of the material could be provided in other embodiments through the use of elastics, embossed material, and/or in any other suitable manner.

Turning now to FIGS. 2A and 2B, another exemplary embodiment 110 of a disposable incontinent underwear garment is depicted. In this example, garment 110 comprises a front panel 112 having a top end 114, a bottom end 116, and two side ends 118 and 120. Further, the garment comprises a back panel 132 having a top end 134, a bottom end 136 and sides 138 and 140. The garment includes a crotch region 130 comprising bottom ends 116 and 136 of the front and back panels, with an absorbent insert or assembly 150 included in the crotch region. When assembled for use by a wearer, sides 118 and 120 are permanently or removably attached to one another such that top ends 114 and 134, which define a waist region of the garment, form a waist opening 128, with leg openings 126A and 126B formed by the front and back panels and crotch region. In this example, leg openings are further defined by leg elastics 152A and 152B, which may comprise any suitable material, such as elastic strands, ribbons, or other material. In this example, the garment defines hip regions 120, 122, 140, and 142. As was noted above, the hip regions may be defined by the front and back panels, which may extend across the front and back sides of the garment in some embodiments. In other embodiments, as indicated by dashed lines 117, 119, 137 and 139, the hip regions may comprise separate panels.

In this embodiment, different areas of stretch 101, 102, 103, 104, 105, and 106 are shown and illustrate that the stretch characteristics of the garment vary between the front and back sides. Namely, in this example, as shown at 101-103, a portion of the front panel between the crotch region and the front waist region is stretchable in a horizontal direction, and as shown at 104-106, portions of the back panel between the crotch region and the back waist region are stretchable in a vertical direction.

In this example, the portions of the front panel that are stretchable extend across from both sides of the front panel, including front side hip regions 122 and 124. Similarly, in this example, the portion of the back panel that is stretchable in the vertical direction also extends from both sides and includes back side hip regions 142 and 144. In other embodiments, the stretch may not necessarily extend from both sides of either panel.

In this embodiment, the horizontal stretch in the front may provide for a better fit for users with larger abdomens. The vertical stretch in the back region may provide for better buttock coverage. Furthermore, absorbent insert 150 may be positioned properly based in this design because the back coverage could be adjusted in the vertical direction while the front portion substantially remains in place on the wearer. As indicated at 146, in this example, a stretchable functional waistband can be included to aid in holding the product up on the wearer. The stretchable functional waistband may comprise embossed material or may comprise other elastic material, such as elastic strands or ribbons. As was noted earlier, however, not all embodiments feature a stretchable waistband and it may accordingly be omitted in some embodiments of the present subject matter.

Although in this example crotch region 130 is not stretchable, in other embodiments, the crotch region may have horizontal, vertical, or biaxial stretch. As was noted above, the amount of stretch that is provided in the crotch region can be adjusted for optimal user experience to avoid sagging, drooping or other issues.

Figure 3:
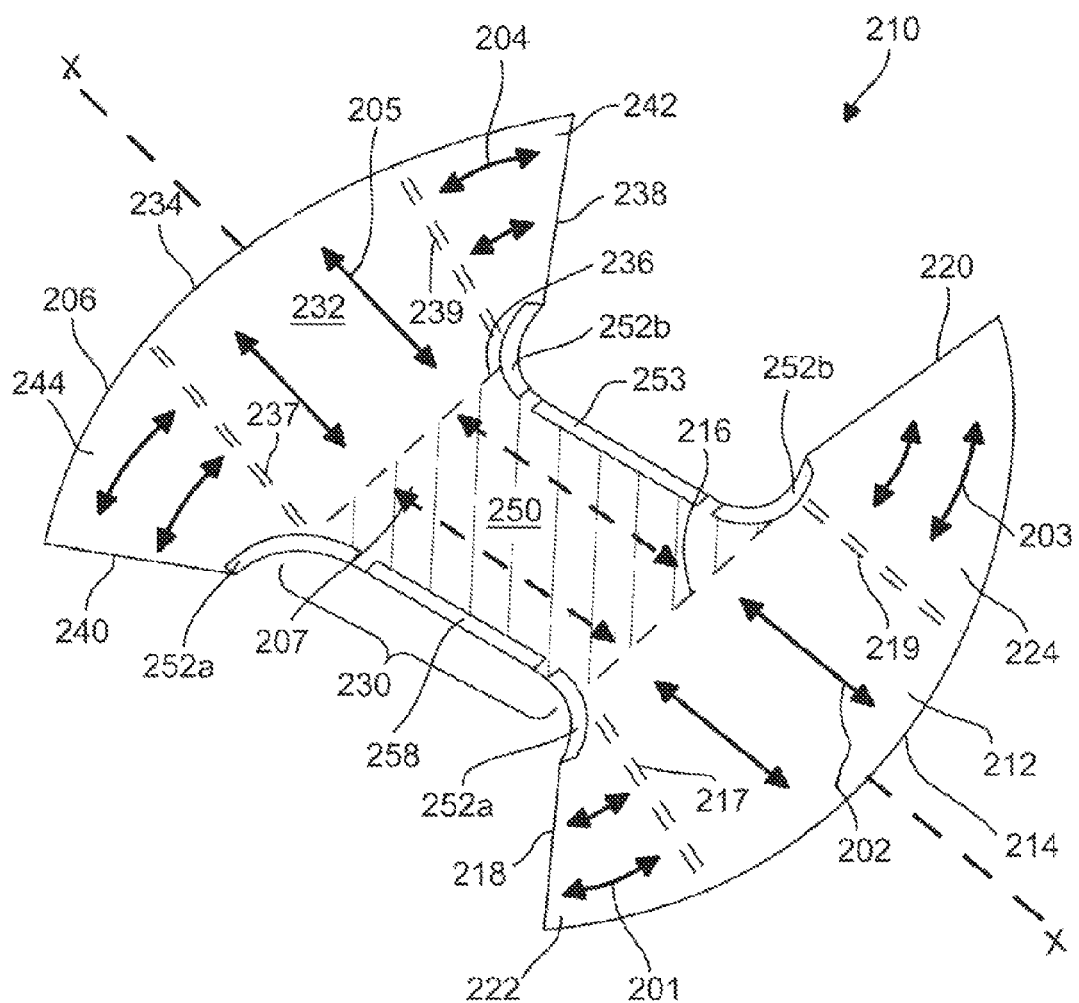
FIG. 3 is a perspective view of another exemplary embodiment of a disposable undergarment as shown in a partially-laid flat orientation.

FIG. 3 is a diagram showing a partial perspective view of another exemplary undergarment 210 in a substantially laid-flat configuration. In this example, the garment features areas of vertical stretch 202 and 205, located at respective portions of front panel 212 and back panel 232. Additionally, areas of horizontal stretch 201, 203, 204, and 206 are shown in front hip region 222 and 224 and back hip regions 242 and 244. In this example, crotch area 230 can be seen more clearly, along with the extent of absorbent insert 250 with crotch elastics 253 shown along the side edges of insert 250. Generally, the areas of directional stretch in this example are similar to those of the embodiment shown in FIGS. 1A-1B.

However, in this example, crotch area 230 is characterized by vertical stretch characteristic 250. For instance, absorbent insert 250 may be formed of stretchable material configured to provide vertical stretch. Of course, in other embodiments, crotch area 230 could feature biaxial, horizontal, or other stretch characteristics.

In some embodiments, rather than using separate front and back panels 212 and 232, a continuous piece of material extending through crotch region 230 and comprising areas corresponding to front panel 212 and 232 could be utilized. This could be especially advantageous if vertical stretch were desired entirely through the crotch region. In such a construction, the front panel, back panel, and crotch region could be defined by a piece of material extending from back waist edge 234 to front waist edge 214, with the sides thereof following a line defined by 237/217 and 239/219 and the respective sides of crotch region 230.

Hip regions 222, 224, 238, and 240 may each comprise a separate piece of material bonded or otherwise joined to respective portions of the continuous piece of material. However, in other embodiments, hop regions 222/244 and hip regions 224/242 could each comprise a unitary piece of material.

Such construction techniques could be applicable to embodiments using separate front and back panels, as well. For instance, in some embodiments, an undergarment may be formed of four pieces of material (front panel, back panel, right hip region, left hip region) plus an absorbent insert, liners, covers, and/or other components. In other embodiments, an undergarment may be formed of six pieces of material (front panel, back panel, right front hip region, right back hip region, left front hip region, left back hip region) plus an absorbent insert, liners, covers, and/or other components. In still further embodiments, the garment could comprise a front panel comprising one or both front hip regions and a back panel comprising one or both back hip regions, plus an absorbent insert, liners, covers, and/or other components. Other variations in materials and component pieces can be envisioned, as well.

The underlying components of the exemplary absorbent articles herein can be assembled in any suitable manner. For instance, front, back, and hip/side panels may be joined through one or more of adhesive, thermal point, and/or ultrasonic bonding. Returning briefly to FIG. 1 and exemplary garment 10, for example, a portion of material corresponding to the portion front panel 12 comprising vertical stretch area 2 could be pressure-bonded to portions of material corresponding to hip panels comprising stretch areas 1 and 3, respectively. Similar techniques could be used to assemble rear portions of exemplary garment 10. Then, an absorbent assembly could be bonded to the front and back panels to extend between bottom edges 16 and 36 to define crotch region 30. Finally, side seams could be formed by bonding edges 18 and 40 and 20 and 38. Of course, other techniques could be used to assemble multiple garments simultaneously or in a high-production environment, and the above example is for purposes of illustration only.

The material particularly shown and described above is not meant to be limiting, but instead serves to show and teach various exemplary implementations of the present subject matter. As set forth in the attached claims, the scope of the present invention includes both combinations and sub-combinations of various features discussed herein, along with such variations and modifications as would occur to a person of skill in the art.

What is claimed:

1. A disposable incontinent underwear product comprising:
    a front panel having a top end, a bottom end, and two respective sides, the front panel defining a front waist region of a disposable incontinent underwear product at the top end of the front panel;
    a back panel having a top end, a bottom end, and two respective sides, the back panel defining a back waist region of the disposable incontinent underwear product at the top end of the back panel; and
    an absorbent insert positioned in a crotch region of the disposable incontinent underwear product, the crotch region comprising the bottom ends of the front panel and back panel, wherein the absorbent insert is secured to the front and back panels;
    wherein the front and back panels, when joined at respective sides, define hip regions of the disposable incontinent underwear product;
    wherein a portion of the front panel lying at least between the crotch region and the front waist region is stretchable in a vertical direction and portions of the front panel defining the hip regions are stretchable in a horizontal direction;
    wherein a portion of the back panel lying at least between the crotch region and the back waist region is stretchable in a vertical direction and portions of the back panel defining the hip regions are stretchable in a horizontal direction;
    wherein each portion of the front and back panels that is stretchable in the vertical direction is substantially not stretchable in the horizontal direction; and
    wherein each portion of the front and back panels that is stretchable in the horizontal direction is substantially not stretchable in the vertical direction.

2. The disposable incontinent underwear product set forth in claim 1, wherein the front and back panels comprise elastic material embossed to impart the respective horizontal and vertical extensibility.

3. The disposable incontinent underwear product set forth in claim 1, wherein the crotch region is stretchable in at least one of the horizontal and vertical direction.

4. The disposable incontinent underwear product set forth in claim 1, further comprising an elastic waistband stretchable in the horizontal direction and positioned at the top ends of the front panel and back panel.

5. The disposable incontinent underwear product as set forth in claim 1, wherein at least one of the front and back panels comprise at least one tear line substantially parallel to a side edge of the product, wherein the tear line comprises an area wherein the material has been conditioned to facilitate separation of the material along the tear line.

6. The disposable incontinent underwear product as set forth in claim 1, wherein the front and back panels comprise an outer cover of the product.

7. The disposable incontinent underwear product as set forth in claim 1, wherein a single piece of material extending from the front waist region to the rear waist region comprises the front and back panels.

8. The disposable incontinent underwear product as set forth in claim 7, wherein the area of vertical stretch extends through the crotch region of the product.

9. The disposable incontinent underwear product as set forth in claim 7, wherein the portion of the front panel lying between the crotch region and the front waist region is formed from a separate piece of material from the portions of the front panel defining a hip region.

10. The disposable incontinent underwear product as set forth in claim 1, wherein the absorbent insert is permanently secured to the front and back panels.

11. The disposable incontinent underwear product as set forth in claim 1, wherein the absorbent insert is releasably secured to the front and back panels.

12. A disposable incontinent underwear product comprising:
 a front panel defining a top and bottom end and two respective sides, the front panel defining a front waist region of a disposable incontinent underwear product at the top end of the front panel;
 a back panel having a top end, a bottom end, and two respective sides, the back panel defining a back waist region of the disposable incontinent underwear product at the top end of the back panel; and
 an absorbent insert positioned in a crotch region of the disposable incontinent underwear product, the crotch region comprising the bottom ends of the front panel and back panel, wherein the absorbent insert is secured to the front and back panels;
 wherein the front and back panels, when joined at respective sides, define hip regions of the disposable incontinent underwear product;
 wherein a portion of the front panel lying at least between the crotch region and the front waist region is stretchable in a horizontal direction;
 wherein a portion of the back panel lying at least between the crotch region and the back waist region is stretchable in a vertical direction;
 wherein each portion of the front and back panels that is stretchable in the vertical direction is substantially not stretchable in the horizontal direction; and
 wherein each portion of the front and back panels that is stretchable in the horizontal direction is substantially not stretchable in the vertical direction.

13. The disposable incontinent underwear product set forth in claim 12, wherein the front and back panels comprise elastic material embossed to impart the respective horizontal and vertical extensibility.

14. The disposable incontinent underwear product set forth in claim 12, wherein the crotch region is stretchable in at least one of the horizontal and vertical direction.

15. The disposable incontinent underwear product set forth in claim 12, further comprising an elastic waistband stretchable in the horizontal direction and positioned at the top ends of the front panel and back panel.

16. The disposable incontinent underwear product as set forth in claim 12, wherein the front and back panels comprise an outer cover of the product.

17. The disposable incontinent underwear product as set forth in claim 12, wherein at least one of the front and back panels comprise at least one tear line substantially parallel to a side edge of the product, wherein the tear line comprises an area wherein the material has been conditioned to facilitate separation of the material along the tear line.

\* \* \* \* \*